(12) United States Patent
Lee

(10) Patent No.: US 8,781,991 B2
(45) Date of Patent: Jul. 15, 2014

(54) EMOTION RECOGNITION APPARATUS AND METHOD

(75) Inventor: Ho-Sub Lee, Seoul (KR)

(73) Assignee: Samsung Electronics Co., Ltd., Suwon-si (KR)

(*) Notice: Subject to any disclaimer, the term of this patent is extended or adjusted under 35 U.S.C. 154(b) by 304 days.

(21) Appl. No.: 13/297,139

(22) Filed: Nov. 15, 2011

(65) Prior Publication Data

US 2013/0018837 A1 Jan. 17, 2013

(30) Foreign Application Priority Data

Jul. 14, 2011 (KR) ........................ 10-2011-0070000

(51) Int. Cl.
*G06F 9/44* (2006.01)
*G06N 7/02* (2006.01)
*G06N 7/06* (2006.01)

(52) U.S. Cl.
USPC .......................................................... 706/52

(58) Field of Classification Search
None
See application file for complete search history.

(56) References Cited

U.S. PATENT DOCUMENTS

| | | | |
|---|---|---|---|
| 7,337,017 B2 | 2/2008 | Dinges et al. | |
| 7,465,503 B2 * | 12/2008 | Lee et al. | 429/509 |
| 8,204,747 B2 * | 6/2012 | Kato et al. | 704/254 |
| 8,297,754 B2 * | 10/2012 | Kwag et al. | 352/243 |
| 8,615,193 B2 * | 12/2013 | Lee et al. | 455/12.1 |
| 2005/0114142 A1 | 5/2005 | Asukai et al. | |
| 2007/0135689 A1 | 6/2007 | Asukai et al. | |
| 2010/0302254 A1 | 12/2010 | Min et al. | |

FOREIGN PATENT DOCUMENTS

| | | |
|---|---|---|
| KR | 10-2005-0039332 A | 4/2005 |
| KR | 10-2005-0049370 A | 5/2005 |
| KR | 10-2010-0129122 A | 12/2010 |

OTHER PUBLICATIONS

Grifantini, Kristina, "Sensor Detects Emotions through the Skin," Biomedicine, Technology Review (Published by MIT), Oct. 26, 2010, Web URL:<http://www.technologyreview.com/biomedicine/26615/page1>, (4 pages, in English).
Hill, Dan, "Emotionomics: Leveraging Emotions for Business Success," 2010, Kogan Page, USA, (369 pages, in English).
Lee, Hosub, et al., "Towards Unobtrusive Emotion Recognition for Affective Social Communication," SAIT, Samsung Electronics Co., Ltd., Yongin-si, Republic of Korea (5 pages, in English).
Russell, James A., "A Circumplex Model of Affect," Journal of Personality and Social Psychology, 1980, pp. 1161-1178, vol. 39, No. 6.
Zimmermann, Philippe, "Affective Computing—A Rationale for Measuring Mood with Mouse and Keyboard," 2003, pp. 1-10, Swiss Federal Institute of Technology, Zurich, Switzerland.

* cited by examiner

*Primary Examiner* — Michael B Holmes
(74) *Attorney, Agent, or Firm* — NSIP Law

(57) ABSTRACT

An emotion recognition apparatus and method are provided. The emotion recognition apparatus acquires a first emotion factor and a second emotion factor of an emotion model. An emotional state of a user is estimated based on the first emotion factor and the second emotion factor. The emotion recognition apparatus may also acquire a third emotion factor of the emotion model.

36 Claims, 12 Drawing Sheets

| 401 | 402 | | | |
|---|---|---|---|---|
| IT EXAMPLE | | UC EXAMPLE | | |
| POSITIVE | NEGATIVE | LOCATION | | SCHEDULE |
| HAPPY | SAD | WEDDING HALL | +1.5 | EXAM | -2 |
| JOY | GLOOMY | FUNERAL HALL | -3 | TRAVEL | +4 |
| :) | :( | ⋮ | ⋮ | ⋮ | ⋮ |
| ⋮ | ⋮ | | | | |

EMOTION RECOGNITION APPARATUS AND METHOD

CROSS-REFERENCE TO RELATED APPLICATION(S)

This application claims the benefit under 35 U.S.C. §119(a) of Korean Patent Application No. 10-2011-0070000, filed on Jul. 14, 2011, in the Korean Intellectual Property Office, the entire disclosure of which is incorporated herein by reference for all purposes.

BACKGROUND

1. Field

The following description relates to a technique for estimating the emotional state of a user of a terminal.

2. Description of the Related Art

Recently, smart phones or tablet PCs have been designed to have hardware performance able to provide a variety of functions and services. In particular, a number of smart phones or tablet PCs provide context-awareness services that are characterized by providing various functions in consideration of the context of a user. Even though context awareness is still at a relatively early stage, high-quality intelligent services that involve complicated reasoning processes may become available in the near future.

In the meantime, studies from fields such as brain science or psychology show that emotions have a greater influence than reason on the human thinking process. Since the amount of time that it takes for the emotional brain to process sensory information is only about one fifth of the amount of time that it takes for the rational brain to process sensory information, people typically feel an emotion before coming up with a thought or making a decision. Accordingly, it may be argued that one's emotional state is reflected in his or her desire or decision-making process.

If a mobile terminal is able to estimate the emotion of a user, the mobile terminal may provide more relevant services such as, for example, providing services suitable for the current emotional state of the user.

SUMMARY

A first emotion factor of an emotion model may be acquired based on at least one first-level data that is a part of sensing data obtained from a terminal. The first-level data may be of the same dimension as the sensing data. A second emotion factor of the emotion model may be acquired based on at least one second-level data that is another part of the sensing data. The second-level data may be of a different dimension from the sensing data, and may be mapped to the meaning of the sensing data. A third emotion factor of the emotion model may be acquired based on a user's personality trait.

An emotional state of the user may be estimated based on the first and second emotion factors or based on the first, second, and third emotion factors.

In one general aspect, there is provided an emotion recognition apparatus, including: a data collection unit to collect sensing data from a terminal; a first emotion value acquisition unit to acquire a first emotion value corresponding to a first axis of a multidimensional emotion model based on an amount or an intensity of the sensing data; a second emotion value acquisition unit to acquire a second emotion value corresponding to a second axis of the multidimensional emotion model based on a meaning of the sensing data; and an emotion estimation unit to estimate an emotional state of a user based on the first emotion value and the second emotion value.

The first emotion value acquisition unit may further acquire first-level data relating to the user's level of arousal by analyzing the amount or the intensity of the sensing data, and acquire the first emotion value based on the first-level data.

The first emotion value acquisition unit may further calculate a touch activeness (TA) level by analyzing the amount or the intensity of sensing data relating to one or more touch inputs detected from the terminal, and calculate the first emotion value based on the calculated TA level.

The first emotion value acquisition unit may further calculate a device movement (DM) level by analyzing the amount or the intensity of sensing data relating to the movement of the terminal, and calculate the first emotion value based on the calculated DM level.

The first emotion value acquisition unit may further calculate a TA level by analyzing the amount or the intensity of sensing data relating to one or more touch inputs detected from the terminal, calculate a DM level by analyzing the amount or the intensity of sensing data relating to the movement of the terminal, and calculate the first emotion value based on a weighted sum of the calculated TA level and the calculated DM level.

The second emotion value acquisition unit may further acquire second-level data relating to valence of the user by analyzing the meaning of the sensing data, and acquire the second emotion value based on the second-level data.

The second emotion value acquisition unit may further calculate an input text (IT) level by analyzing the meaning of sensing data relating to a user input that is entered to the terminal, and calculate the second emotion value based on the calculated IT level.

The user input may include at least one selected from the group of text data, audio data, video data, an emoticon, and the like.

The second emotion value acquisition unit may further calculate a user context (UC) level by analyzing the meaning of sensing data relating to a context of the user, and calculate the second emotion value based on the calculated UC level.

The context may include at least one selected from the group of a location of the user, a schedule of the user, and the like.

The second emotion value acquisition unit may further calculate an IT level by analyzing the meaning of sensing data relating to a user input that is entered to the terminal, calculate a UC level by analyzing the meaning of sensing data relating to context of the user, and calculate the second emotion value based on a weighted sum of the calculated IT level and the calculated UC level, wherein the user input may include at least one selected from the group of text data, audio data, video data, an emoticon, and the like; and wherein the context may include at least one selected from the group of a location of the user, a schedule of the user, and the like.

The first emotion value and the second emotion value may be values of Russell's emotion model, or may be values of Watson-Tellegen's emotion model.

The TA level may be calculated with respect to a period of time for which a touch input is detected, touch counts detected during the period of time, a touch movement distance during the period of time, a heavy touch movement count during the period of time, and a number of characters entered during the period of time, wherein the heavy touch movement count is calculated according to a number of substantially continuous touches that include more than a predetermined number of changes in direction.

The DM level may be calculated with respect to a period of time for which a touch input is detected, a value representing x-axis acceleration of the terminal, a value representing y-axis acceleration of the terminal, and a value representing z-axis acceleration of the terminal.

The IT level may be calculated with respect to a period of time for which a touch input is detected, a ratio of positive user inputs to all user inputs that are entered during the period of time, and a ratio of negative user inputs to all the user inputs that are entered during the period of time.

The UC level may be calculated with respect to an elapsed time for a touch input, a duration for which the user remains at a location, a value representing positive or negative context of the location, and a value representing positive or negative context of a schedule of the user.

In another general aspect, there is provided an emotion recognition apparatus, including: a data collection unit to collect sensing data from a terminal; a first emotion value acquisition unit to acquire a first emotion value corresponding to a first axis of a multidimensional emotion model based on an amount or an intensity of the sensing data; a second emotion value acquisition unit to acquire a second emotion value corresponding to a second axis of the multidimensional emotion model based on a meaning of the sensing data; a third emotion value acquisition unit to acquire a third emotion value corresponding to a user's personality trait; and an emotion estimation unit to estimate an emotional state of the user based on at least two selected from the group of the first emotion value, the second emotion value, and the third emotion value.

The emotion estimation unit may further estimate an internal emotional state of the user based on the first and second emotion values, and estimate an external emotional state of the user based on the first, second, and third emotion values.

The emotion recognition apparatus may further include an emotion provision unit to output data regarding the estimated internal emotional state and data regarding the estimated external emotional state of the user.

The emotion provision unit may further output the data regarding the estimated internal emotional state of the user to a user interface of the terminal, and output the data regarding the estimated external emotional state of the user to an external device.

In another general aspect, there is provided an emotion recognition method, including: collecting sensing data from a terminal; acquiring a first emotion value corresponding to a first axis of a multidimensional emotion model based on an amount or an intensity of the sensing data; acquiring a second emotion value corresponding to a second axis of the multidimensional emotion model based on a meaning of the sensing data; and estimating an emotional state of a user based on the first emotion value and the second emotion value.

In another general aspect, there is provided an emotion recognition method, including: collecting sensing data from a terminal; acquiring a first emotion value corresponding to a first axis of a multidimensional emotion model based on an amount or an intensity of the sensing data; acquiring a second emotion value corresponding to a second axis of the multidimensional emotion model based on a meaning of the sensing data; acquiring a third emotion value corresponding to a user's personality trait; and estimating an emotional state of the user based on at least two selected from the group of the first emotion value, the second emotion value, and the third emotion value.

The estimating the emotional state of the user may include estimating an internal emotional state of the user based on the first and second emotion values; and estimating an external emotional state of the user based on the first, second, and third emotion values.

The emotion recognition method may further include outputting the estimated internal emotional state and the estimated external emotional state of the user, wherein the outputting of the estimated internal emotional state and the estimated external emotional state of the user comprises outputting the estimated internal emotional state of the user to a user interface of the terminal, and outputting the estimated external emotional state of the user to an external device.

Other features and aspects may be apparent from the following detailed description, the drawings, and the claims.

BRIEF DESCRIPTION OF THE DRAWINGS

FIG. 4 is a diagram illustrating an example of a database (DB).

Figure 1:
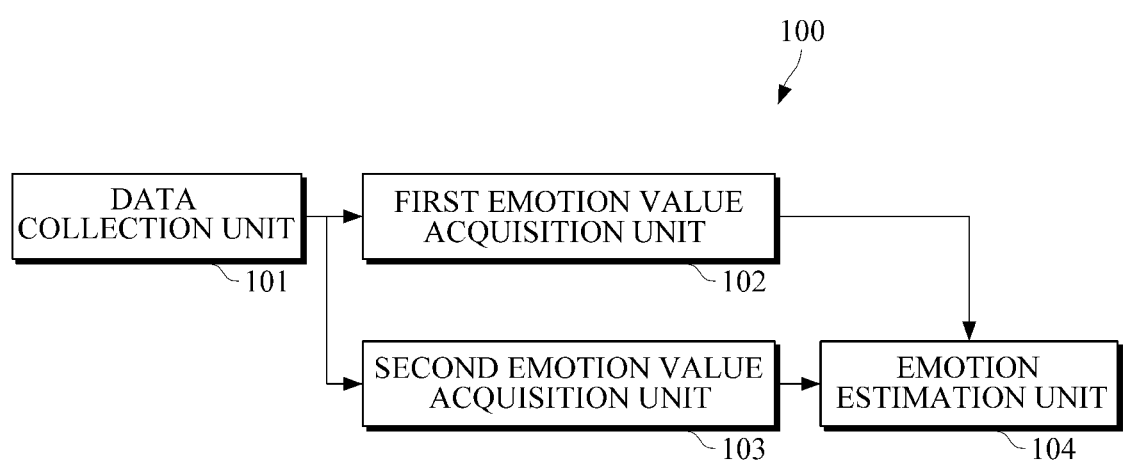
FIG. 1 is a diagram illustrating an example of an emotion recognition apparatus.

Throughout the drawings and the detailed description, unless otherwise described, the same drawing reference numerals should be understood to refer to the same elements, features, and structures. The relative size and depiction of these elements may be exaggerated for clarity, illustration, and convenience.

DETAILED DESCRIPTION

The following description is provided to assist the reader in gaining a comprehensive understanding of the methods, apparatuses, and/or systems described herein. Accordingly, various changes, modifications, and equivalents of the methods, apparatuses, and/or systems described herein may be suggested to those of ordinary skill in the art. Also, descriptions of well-known functions and constructions may be omitted for increased clarity and conciseness.

FIG. 1 illustrates an example of an emotion recognition apparatus.

Referring to FIG. 1, emotion recognition apparatus 100 may be included in or implemented as a fixed terminal or a mobile terminal. Examples of the fixed terminal include a personal computer (PC), a television (TV), and various other home appliances. Examples of the mobile terminal include a smart phone, a tablet PC, a mobile phone, a personal digital assistant (PDA), a portable multimedia player (PMP), an MP3 player, and the like.

The emotion recognition apparatus 100 may be a part of a fixed or mobile terminal. For example, the emotion recognition apparatus 100 may be implemented as a hardware element or a software element of a fixed or mobile terminal.

The emotion recognition apparatus 100 includes a data collection unit 101, a first emotion value acquisition unit 102, a second emotion acquisition unit 103, and an emotion estimation unit 104.

The data collection unit 101 may collect sensing data from a terminal. For example, the sensing data may include various data that is obtained by various sensors of the terminal.

The data collection unit 101 may include a hardware sensor and/or a software sensor. For example, the data collection unit 101 may collect information relating to the touch input on the touch screen of the terminal (for example, a touch pattern), a 3-axis accelerometer value (for example, the state of movement of the terminal), a global positioning system (GPS) coordinate (for example, current location), pressure, illumination, outside temperature, sound, and the like, using a hardware sensor. As a further example, the data collection unit 101 may collect data regarding the types of applications or functions currently being executed on the terminal; characters, audio data, video data, and/or emoticons inputted by a user; events that are registered in a scheduler or calendar program by the user; weather information available on the internet; and the like, using a software sensor.

The first emotion value acquisition unit 102 may acquire a first emotion value that corresponds to an axis (i.e., a first axis) of a multi-dimensional emotion model. For example, the first emotion value acquisition unit 102 may acquire an arousal value, with regard to Russell's emotion model, as the first emotion value. As another example, the first emotion value acquisition unit 102 may acquire an intensity value, with regard to Watson-Tellegen's emotion model, as the first emotion value.

The first emotion value acquisition unit 102 may acquire the first emotion value in consideration of the amount or intensity of the sensing data provided by the data collection unit 101. For example, if the sensing data is touch information obtained with respect to the touch screen of the terminal, the term 'amount or intensity of sensing data' may indicate the number or intensity of touch inputs detected from the touch screen of the terminal. As another example, if the sensing data is information regarding one or more characters entered by the user, the term 'amount or intensity of sensing data' may indicate the number of input strings entered by the user or the number of characters or words included in each input string. The first emotion value acquisition unit 102 may acquire the first emotion value by analyzing the amount or intensity of the sensing data.

For example, the first emotion value acquisition unit 102 may calculate a touch activeness (TA) level by analyzing the amount or intensity of sensing data relating to one or more touch inputs detected from the terminal, and the first emotion value acquisition unit 102 may calculate the first emotion value based on the calculated TA level.

In another example, the first emotion value acquisition unit 102 may calculate a device movement (DM) level by analyzing the amount or intensity of sensing data relating to the movement of the terminal, and the first emotion value acquisition unit 102 may calculate the first emotion value based on the calculated DM level.

In another example, the first emotion value acquisition unit 102 may calculate a TA level by analyzing the amount or intensity of the sensing data relating to one or more touch inputs that are detected from the terminal, and a DM level by analyzing the amount or intensity of the sensing data relating to the movement of the terminal. The first emotion value acquisition unit 102 may calculate the first emotion value based on a weighted sum of the calculated TA level and the calculated DM level.

The acquisition of the first emotion value is further described below.

The second emotion value acquisition unit 103 may acquire a second emotion value that corresponds to another axis (i.e., a second axis) of a multi-dimensional emotion model. For example, the second emotion value acquisition unit 103 may acquire a valence value, with regard to Russell's emotion model, as the second emotion value. As another example, the second emotion value acquisition unit 103 may acquire a valenced reaction value, with regard to OCC's emotion model, as the second emotion value.

The second emotion value acquisition unit 103 may acquire the second emotion value in consideration of the meaning of the sensing data provided by the data collection unit 101. For example, the term 'meaning of sensing data' may indicate the sense or context that may be extracted from sensing data. As an example, if the sensing data is a string "I had a great time today," the meaning of the sensing data may be determined as 'joy.' The second emotion value acquisition unit 103 may acquire the second emotion value by analyzing the meaning sensing data.

For example, the second emotion value acquisition unit 103 may calculate an input text (IT) level by analyzing the meaning of sensing data relating to a user input that is entered to the terminal, and the second emotion value acquisition unit 103 may calculate the second emotion value based on the calculated IT level. In this example, the user input may include at least one of text, voice, video, and an emoticon that are entered by the user.

In another example, the second emotion value acquisition unit 103 may calculate a user context (UC) level by analyzing the meaning of sensing data relating to the context of the terminal, and the second emotion value acquisition unit 103 may calculate the second emotion value based on the calculated UC level. In this example, the context of the terminal may be the location and the schedule of the user, weather information, or the like.

In another example, the second emotion value acquisition unit 103 may calculate an IT level by analyzing the meaning of sensing data relating to a user input that includes at least one of text, voice, video, and an emoticon, and the second emotion value acquisition unit 103 may calculate a UC level by analyzing the meaning of sensing data relating to at least one of the location and the schedule of the user. The second emotion value acquisition unit 103 may calculate the second emotion value based on a weighted sum of the calculated IT level and the calculated UC level.

The acquisition of the second emotion value is further described below.

The emotion estimation unit 104 may estimate the emotional state of the user based on the first and second emotion values, which are provided by the first and second emotion value acquisition units 102 and 103, respectively. For example, the emotion estimation unit 104 may map the first and second emotion values onto X- and Y-axes, respectively, of a two-dimensional (2D) emotion model.

Figure 2:
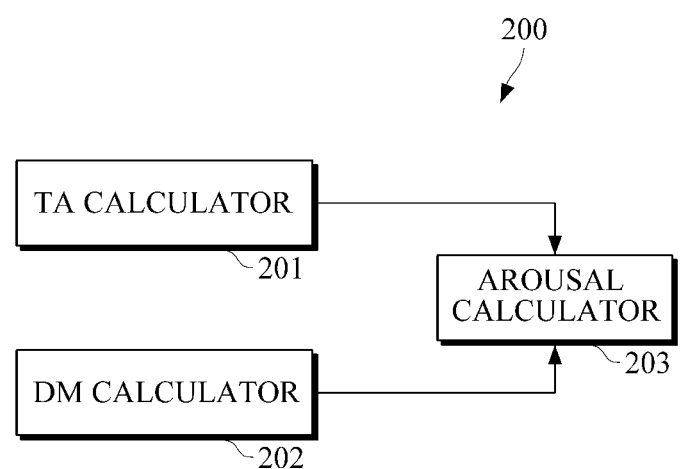
FIG. 2 is a diagram illustrating an example of a first emotion value acquisition unit.

FIG. 2 illustrates an example of the first emotion value acquisition unit 102.

The acquisition of the first emotion value is described with reference to FIGS. 1 and 2.

Referring to FIGS. 1 and 2, in response to the user manipulating the touch screen of the terminal, the data collection unit 101 may collect touch input information from the touch screen of the terminal, and the first emotion value acquisition unit 102 or a first emotion value acquisition unit 200 may be activated. The first emotion value acquisition unit 102 or 200 may calculate the first emotion value based on at least one first-level data. For example, the term 'first-level data' may indicate information that may be obtained by measuring the amount or intensity of collected data that is obtained by the data collection unit 101 and then combining the results of the measurement without consideration of the meaning of the collected data. The first-level data may be expressed in the same unit or the same dimension as sensing data.

Referring to FIG. 2, the first emotion value acquisition unit 200 includes a TA calculator 201, a DM calculator 202, and an arousal calculator 203.

The TA calculator 201 may calculate a TA level according to Equation (1):

$$TA = TC + \left\{ \frac{TMD}{t}(HTMC+1) \right\} + TT \quad (1)$$

where TA denotes the TA level, t denotes a duration for which a touch input continues to be detected, touch count (TC) denotes the number of single touches (such as, for example, clicks) that are detected during the time period t, touch movement distance (TMD) denotes a distance of continuous touches (such as, for example, drags) that are detected during the time period t, heavy touch movement count (HTMC) denotes the number of continuous touches including more than N changes in the touch direction (where N denotes an arbitrary natural number selected by the user), and typing throughput (TT) denotes the number of characters that are entered during the time period t. For example, the term 'continuous touch' indicates a touch input that is generated by a user dragging a finger from one position to another position on the touch screen of the terminal, without removing his or her finger from the touch screen.

Referring to Equation (1), the TA level TA may be calculated as the sum of the number of touches that are detected during the time period t (TC), the average speed of continuous touches (TMD/t) or the number of intense continuous touches (HTMC), and the number of characters that are entered during the during the time period t (TT).

The DM calculator 202 may calculate a DM level according to Equation (2):

$$DM = \sqrt{\left(\frac{\sum_{i=1}^{t} AX_i}{t}\right)^2 + \left(\frac{\sum_{i=1}^{t} AY_i}{t}\right)^2 + \left(\frac{\sum_{i=1}^{t} AZ_i}{t}\right)^2} \quad (2)$$

where DM denotes the DM level, t denotes the duration for which a touch input continues to be detected, AXi denotes a X-axis acceleration value of the terminal, AYi denotes a Y-axis acceleration value of the terminal, and AZi denotes a Z-axis acceleration value of the terminal.

Referring to Equation (2), the DM level DM may be calculated as the sum of average acceleration values collected for each of the X-, Y-, and Z-axes during the time period t.

The arousal calculator 203 may calculate an arousal value based on the TA level TA and the DM level DM, as indicated by Equation (3):

$$Arousal = \frac{TA + \alpha DM}{\mu} \quad (3)$$

where Arousal denotes a first emotion value, a denotes a weight (0≤α≤∞), μ denotes a scaling factor $$\left(\mu = \frac{Arousal}{|Arousal_{LimitValue}|}\right)$$

for limiting the arousal value Arousal to a predetermined range. The weight α may be a predetermined value, or may be a value set by the user.

In the example illustrated in FIG. 2, the arousal value Arousal may be calculated as the first emotion value. However, it is noted that the first emotion value is not restricted to the arousal value Arousal. In the example illustrated in FIG. 2, the arousal value Arousal may be calculated as a weighted sum of the TA level TA and the DM level DM. In another example, one of the TA level TA and the DM level DM may be used as the arousal value Arousal, or the arousal value Arousal may be calculated based on various information other than the TA level TA and the DM level DM.

Figure 3:
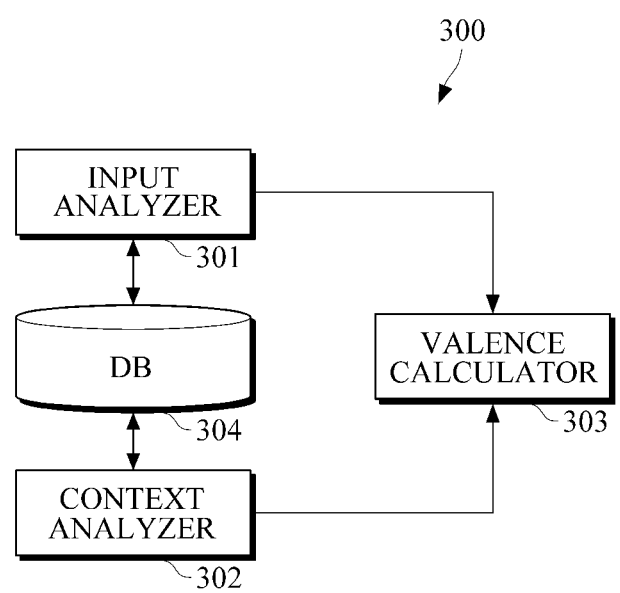
FIG. 3 is a diagram illustrating an example of a second emotion value acquisition unit.

FIG. 3 illustrates an example of the second emotion value acquisition unit 103.

The acquisition of the second emotion value is further described with reference to FIGS. 1 and 3.

Referring to FIGS. 1 and 3, in response to the user manipulating the touch screen of the terminal, the data collection unit 101 may collect touch input information from the touch screen of the terminal, and the second emotion value acquisition unit 103 or a second emotion value acquisition unit 300 may be activated. For example, if the user continues to manipulate the touch screen of the terminal for an amount of time t, the second emotion value acquisition unit 103 or 300 may be activated for an amount of time (t+a), where a denotes an arbitrary natural number. The second emotion value acquisition unit 103 or 300 may calculate the second emotion value based on at least one second-level data. For example, the term 'second-level data' may indicate mapping information of data that is obtained based on the meaning of data collected by the data collection unit 101.

In the example illustrated in FIG. 2, the first-level data may be information that is obtained as a combination of sensing data. For example, the first-level data (i.e., the TA level TA) may be obtained by combining one or more sensing data values (i.e., TC and TMD), for example, by performing an arithmetic operation on the one or more sensing data values. The first-level data may be of the same dimension as the sensing data. In the example illustrated in FIG. 3, the second-level data may be information obtained by analyzing a certain aspect of the sensing data. For example, the second-level data may be information that is of a higher order than sensing data, and that is mapped to sensing data, whereas the first-level data may be obtained simply by combining sensing data.

Referring to FIG. 3, the second emotion value acquisition unit 300 includes an input analyzer 301, a context analyzer 302, a valence calculator 303, and a database (DB) 304.

The input analyzer 301 may calculate an IT level, which indicates the user's level of positiveness or negativeness associated with each user input, according to Equation (4):

$$IT = PKEF - NKEF \quad (4)$$

where IT indicates the IT level, positive keyword emoticon frequency (PKEF) denotes a positive keyword/emoticon frequency, which may be determined by a ratio of positive user inputs to all user inputs that are entered during the time (t+a), and negative keyword emoticon frequency (NKEF) denotes a negative keyword/emoticon frequency, which may be determined by a ratio of negative user inputs to all the user inputs that are entered during the time (t+a). For example, the term 'user input' indicates text, voice, video, or an emoticon that is entered by the user.

The input analyzer 301 may estimate the emotion of the user by analyzing text, voice, video, or an emoticon that is entered to the terminal. User inputs may be classified into positive and negative user inputs in advance, and the results of the classification may be stored in the DB 304.

The context analyzer 302 may calculate a UC level, which indicates the user's level of positiveness or negativeness of context, according to Equation (5):

$$UC = \sum_{i=0}^{\infty} LOC_i \frac{t_i}{t+a} + \sum_{j=0}^{\infty} Schedule_j \frac{t_j}{t+\alpha} \quad (5)$$

where UC denotes the UC level, t indicates an elapsed time for a touch input (1≤t≤∞), a denotes an additionally required time for calculating valence (1≤a≤∞), $t_i$ denotes a duration for which the user stays at a current location i, $LOC_i$ denotes a level of positiveness or negativeness about the current location i where the user is located, $Schedule_j$ denotes a level of positiveness or negativeness about a current schedule j of the user, and $t_j$ denotes a scheduled time for the current schedule j.

The context analyzer 302 may analyze the context of the user (for example, the location and/or the schedule of the user), and may estimate the emotion of the user based on the results of the analysis. Locations or scheduled events may be classified into positive and negative locations or positive and negative scheduled events in advance, and the results of the classification may be stored in the DB 304.

The valence calculator 303 may calculate a valence value based on the IT level IT and the UC level UC, as indicated by Equation (6):

$$Valence = \frac{IT + \alpha UC}{\mu} \quad (6)$$

where Valence denotes the valence value or the second emotion value, a denotes a weight (0≤α≤∞), and μ denotes a scaling factor $$\left(\mu = \frac{Valence}{|Valence_{LimitValue}|}\right)$$

for limiting the valence value Valence to a predetermined range. The weight a may be configured by the user.

In the example illustrated in FIG. 3, the valence value Valence may be calculated as the second emotion value, but the second emotion value is not restricted to the valence value Valence. In the example illustrated in FIG. 3, the valence value Valence may be calculated as a weighted sum of the IT level IT and the UC level UC. In another example, one of the IT level IT and the UC level UC may be used as the valence value Valence, or the valence value Valence may be calculated based on various information other than the IT level IT and the UC level UC.

For example, referring to FIG. 3, the DB 304 may be provided in the second emotion value acquisition unit 300. As another example, the DB 304 may be provided outside the second emotion value acquisition unit 300, such as via an internet connection.

FIG. 4 illustrates an example of the DB 304.

Referring to FIG. 4, DB 400 includes a first DB 401 and a second DB 402. The first DB 401 may be used to determine an IT level, and the second DB 402 may be used to determine a UC level.

The first DB 401 may store various user inputs such as text, voice, video, or emoticons. The various user inputs may be classified into positive and negative user inputs according to a predetermined rule. The predetermined rule may be configured in advance by the user. Referring to FIGS. 3 and 4, the input analyzer 301 may determine whether each user input is positive or negative with reference to the first DB 401.

The second DB 402 may store various locations and various events. The various locations and the various events may each be mapped to positive or negative values. The value to which each location or event is mapped may be configured in advance by the user. Referring to FIGS. 3 and 4, the context analyzer 302 may calculate a UC level that indicates the context of the user by analyzing GPS information or schedule information of the terminal with reference to the second DB 402.

The DB 400 may include more than two DBs, including the first and second DBs 401 and 402. The second DB 402 may also store a variety of other information that may be used for inferring the current situation (for example, weather information), other than locations and scheduled events.

As one example, the DB 400 may be provided in the terminal or may be provided outside the terminal, such as via an internet connection.

Figure 5:
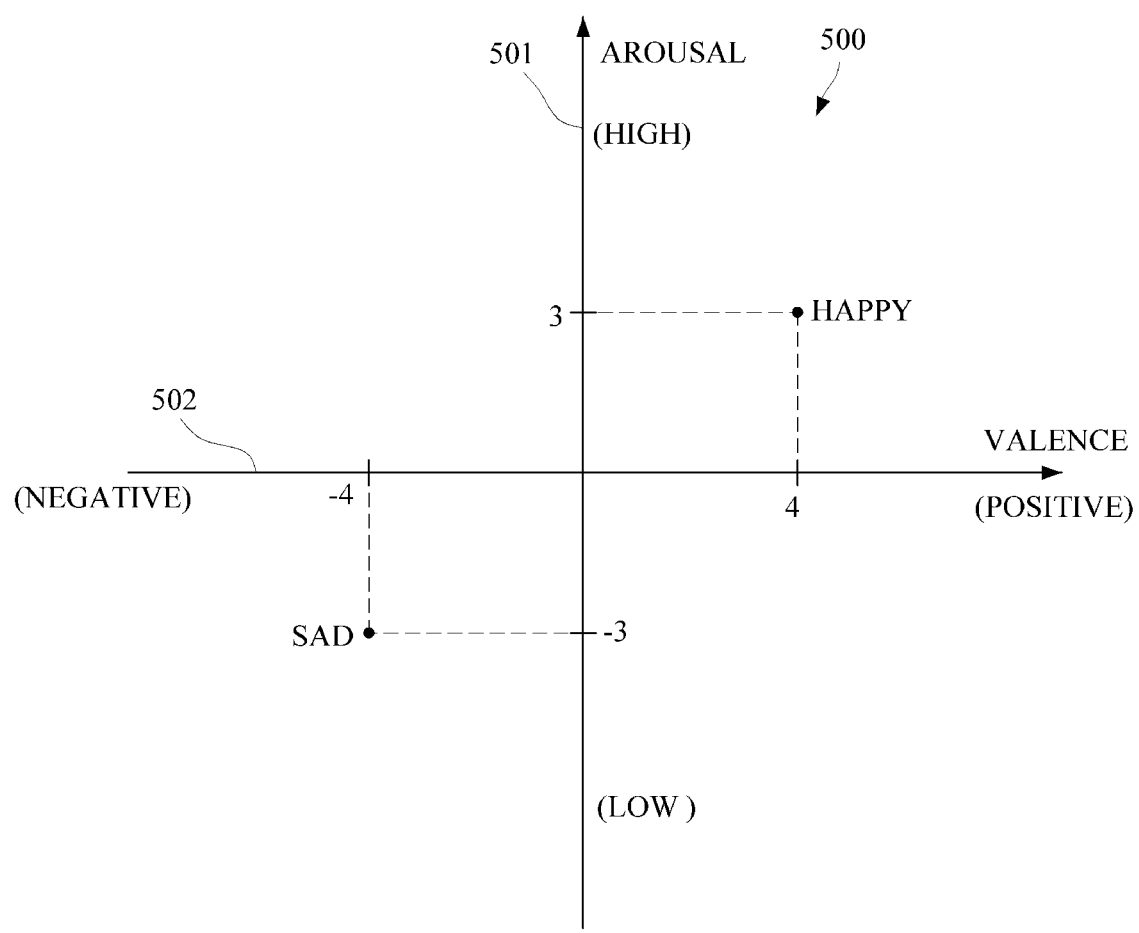
FIG. 5 is a diagram illustrating an example of an emotion model.

FIG. 5 illustrates an example of an emotion model. An example of estimating an emotion is described below with reference to FIG. 5.

Referring to FIG. 5, an emotion model 500 may be defined as a two-dimensional (2D) space having a first axis 501 (i.e., an arousal axis) and a second axis 502 (i.e., a valence axis). Each emotional state may be mapped to a point (x, y) on the emotion model 500.

Referring to FIGS. 1 and 5, the emotion estimation unit 104 may estimate the emotional state of a user by mapping the first emotion value acquired by the first emotion value acquisition unit 102 onto the first axis 501 and mapping the second emotion value acquired by the second emotion value acquisition unit 103 onto the second axis 502. For example, in a case in which the first emotion value is 3 and the second emotion value is 4, the emotional state of the user may be mapped to a point (3, 4), and may thus be determined as corresponding to 'happy.' As another example, in a case in which the first emotion value is −3 and the second emotion value is −4, the emotion of the user may be mapped to a point (−3, −4), and may thus be determined as corresponding to 'sad.'

In the example illustrated in FIG. 5, Russell's emotion model may be used as the emotion model 500. In another example, the Watson-Tellegen's emotion model, which is a three-dimensional (3D) emotion model with X, Y, and Z axes, may be used as the emotion model 500.

Figure 6:
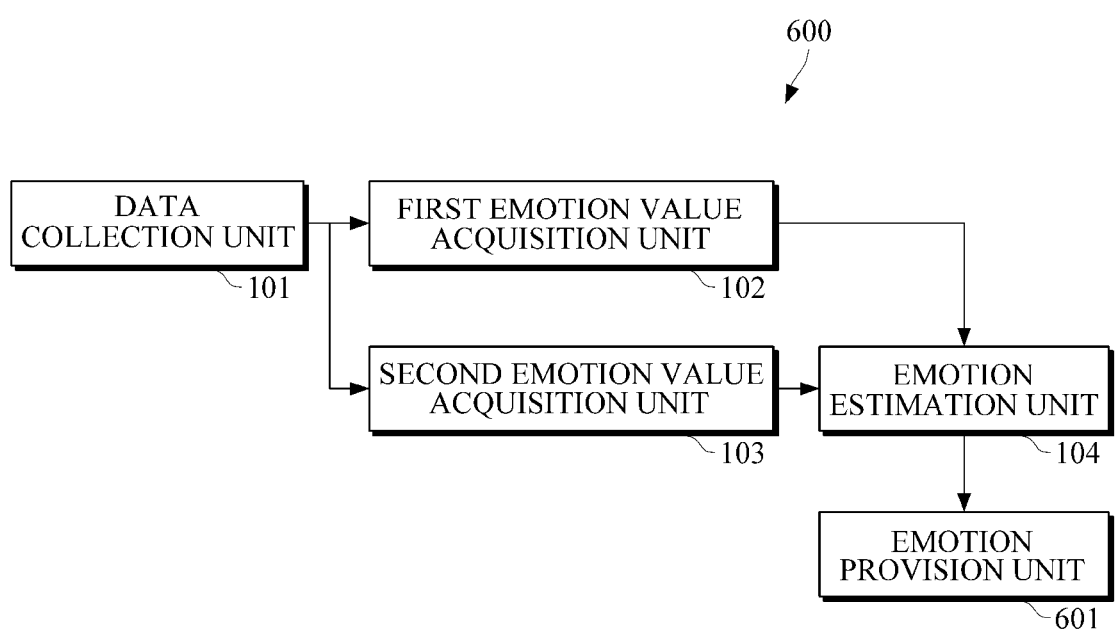
FIG. 6 is a diagram illustrating another example of an emotion recognition apparatus.

FIG. 6 illustrates another example of an emotion recognition apparatus.

Referring to FIG. 6, emotion recognition apparatus 600 includes a data collection unit 101, a first emotion value acquisition unit 102, a second emotion value acquisition unit 103, an emotion estimation unit 104, and an emotion provision unit 601. The data collection unit 101, the first emotion value acquisition unit 102, the second emotion value acquisition unit 103, and the emotion estimation unit 104 are similar to those described with respect to FIG. 1, and thus, detailed descriptions thereof will be omitted.

Referring to FIG. 6, the emotion provision unit 601 may provide the emotional state of a user, which is estimated by the emotion estimation unit 104, to an external device or user. For example, the emotion estimation unit 104 may display an icon that corresponds to the estimated emotional state of the user on a display panel or a touch screen of a terminal. In another example, when the user communicates with another user, the emotion estimation unit 104 may transmit estimated emotional state of the user to the terminal of the other user. In another example, if the user posts a message on a Social Networking Services (SNS) or a website, the emotion provision unit 601 may provide the estimated emotional state of the user so that the estimated emotional state of the user may be automatically transmitted with the message.

Figure 7:
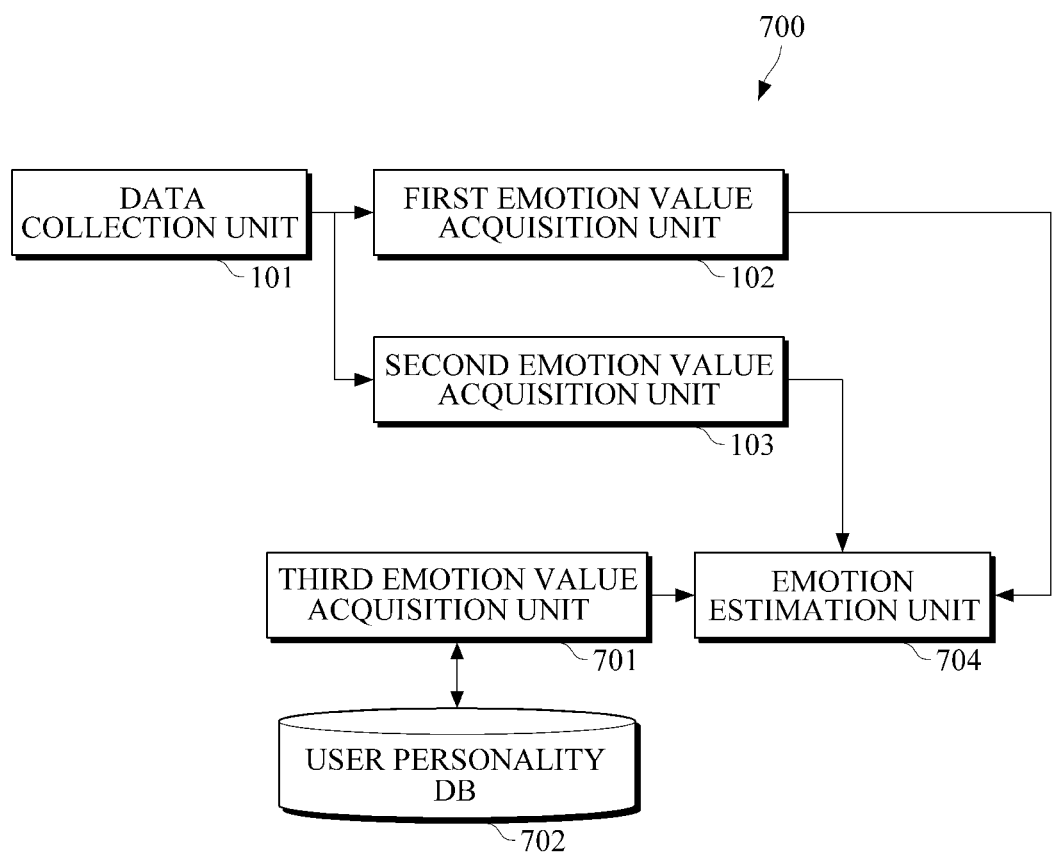
FIG. 7 is a diagram illustrating another example of an emotion recognition apparatus.

FIG. 7 illustrates another example of an emotion recognition apparatus.

Referring to FIG. 7, emotion recognition apparatus 700 includes a data collection unit 101, a first emotion value acquisition unit 102, a second emotion value acquisition unit 103, a third emotion value acquisition unit 701, a user personality DB 702, and an emotion estimation unit 704. The data collection unit 101, the first emotion value acquisition unit 102, and the second emotion value acquisition unit 103 are similar to those described with respect to FIG. 1, and thus, detailed descriptions thereof will be omitted.

Referring to FIG. 7, the third emotion value acquisition unit 701 may acquire a third emotion value that corresponds to a user's personality trait. Values that are mapped to various personality traits may be defined and stored in the user personality DB 702 in advance. For example, in the user personality DB 702, an introvert personality type may be mapped to a value of −1, an intermediate personality type may be mapped to a value of 0, and an extrovert personality type may be mapped to a value of 1.

In the example illustrated in FIG. 7, the user's personality traits may be classified into introversion or extroversion, but the classification of the user's personality traits is not restricted to this particular classification. In another example, various personality traits, other than introversion or extroversion (for example, sense-oriented or intuition-oriented) may be stored in the user personality DB 702.

The emotion estimation unit 704 may estimate the emotional state of the user based on first and second emotion values or based on the first, second, and third emotion values. For example, the emotion estimation unit 704 may estimate the emotional state of the user by mapping the first and second emotion values onto a 2D emotion model (such as, for example, the emotion model 500 illustrated in FIG. 5). In another example, the emotion estimation unit 704 may estimate the emotional state of the user by mapping the first, second, and third emotion values onto a 3D emotion model.

Figure 8:
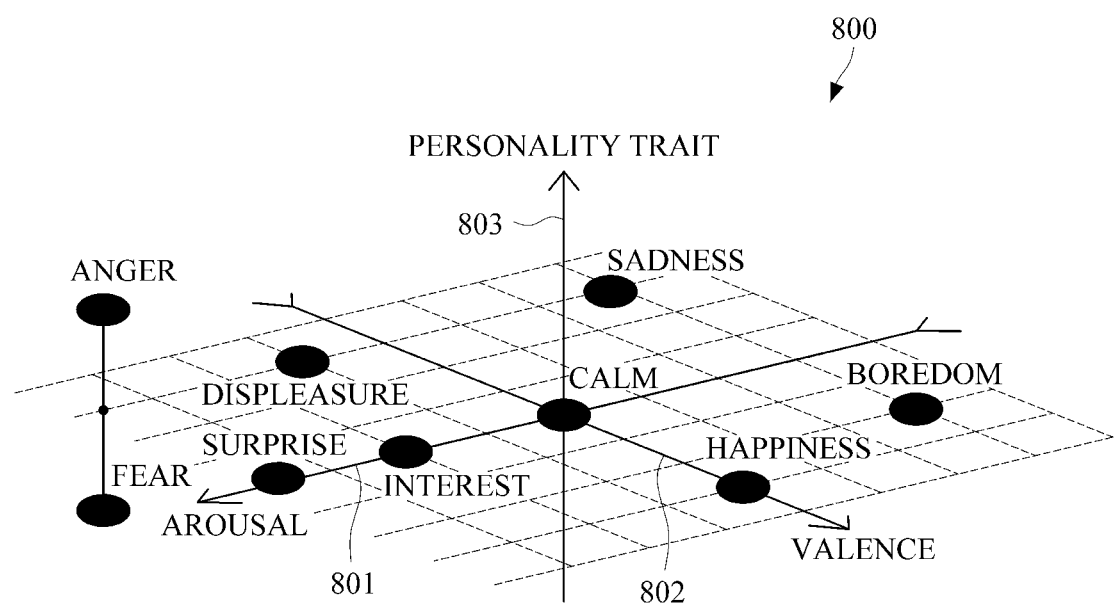
FIG. 8 is a diagram illustrating another example of an emotion model.

FIG. 8 illustrates another example of an emotion model. Another example of estimating an emotion is described below with reference to FIG. 8.

Referring to FIG. 8, an emotion model 800 may be defined as a 3D space having a first axis 801 (i.e., an arousal axis), a second axis 802 (i.e., a valence axis), and a third axis 803 (i.e., a personality trait axis). Each emotional state may be mapped to a point (x, y, z) on the emotion model 800.

Referring to FIGS. 7 and 8, the emotion estimation unit 704 may estimate the emotional state of a user by mapping the first emotion value acquired by the first emotion value acquisition unit 102 onto the first axis 801, mapping the second emotion value acquired by the second emotion value acquisition unit 103 onto the second axis 802, and mapping the third emotion value acquired by the third emotion value acquisition unit 701 onto the third axis 803. For example, in a case in which the first emotion value is 4 and the second emotion value is −3, the emotional state of the user may be identified either as 'anger' or 'fear' according to whether the user is extrovert or introvert.

Figure 9:
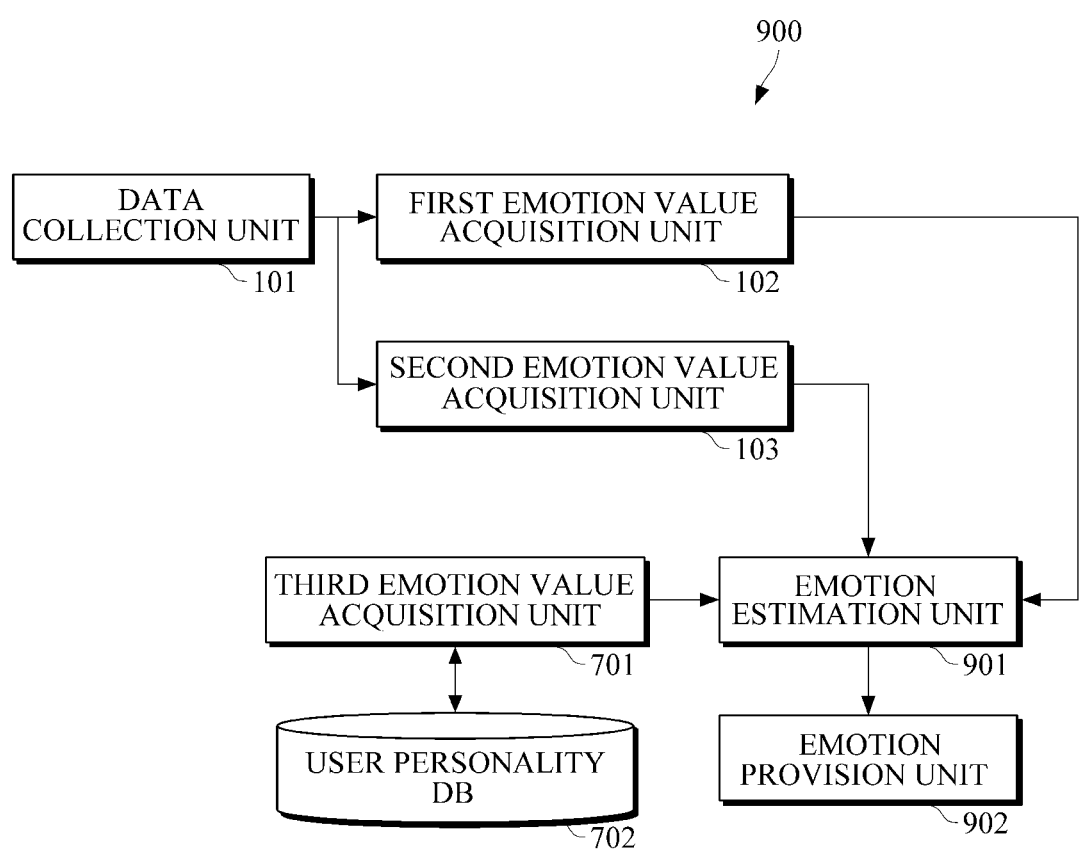
FIG. 9 is a diagram illustrating another example of an emotion recognition apparatus.

FIG. 9 illustrates another example of an emotion recognition apparatus.

Referring to FIG. 9, emotion recognition apparatus 900 includes a data collection unit 101, a first emotion value acquisition unit 102, a second emotion value acquisition unit 103, an emotion estimation unit 901, a third emotion value acquisition unit 701, a user personality DB 702, and an emotion provision unit 902. The data collection unit 101, the first emotion value acquisition unit 102, the second emotion value acquisition unit 103, the third emotion value acquisition unit 701, and the user personality DB 702 are similar to those described with respect to FIGS. 1 and 7, and thus, detailed descriptions thereof will be omitted.

Referring to FIG. 9, the emotion estimation unit 901 may estimate the emotional state of a user based on a first emotion value acquired by the first emotion value acquisition unit 102 and a second emotion value acquired by the second emotion value acquisition unit 103. For example, the emotional state of the user estimated based on the first and second emotion values may be referred to as an internal emotional state.

The emotion estimation unit 901 may estimate the emotional state of the user based on the first and second emotion values and a third emotion value acquired by the third emotion value acquisition unit 701. For example, the emotional state of the user that may be estimated based on the first, second, and third emotion values may be referred to as an external emotional state.

The emotion provision unit 902 may provide the estimated internal emotional state and/or the estimated external emotional state of the user to an external device. For example, the emotion provision unit 902 may provide the estimated internal emotional state of the user to a display panel or a touch screen of a terminal. As another example, the emotion provision unit 902 may provide the estimated external emotional state of the user to another terminal that communicates with the user's terminal, or vice versa.

Figure 10:
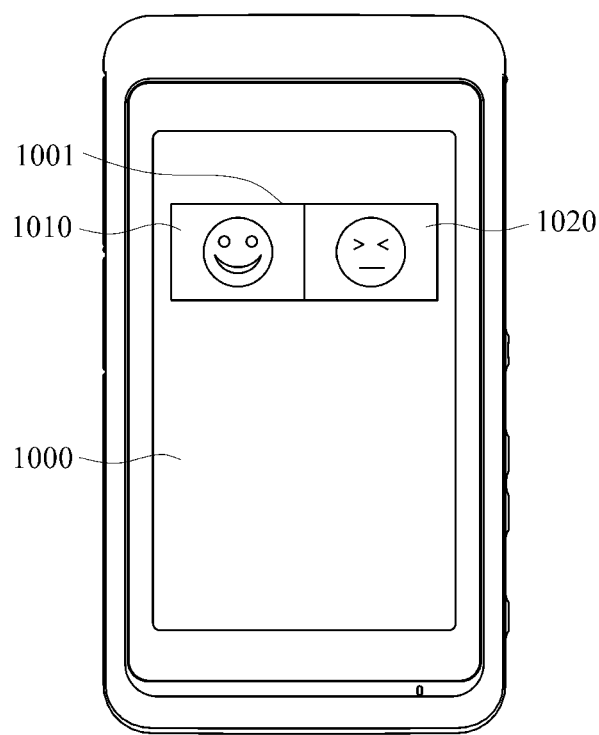
FIG. 10 is a diagram illustrating an example of a terminal to which an emotion recognition apparatus is applied.

FIG. 10 illustrates an example of a terminal to which an emotion recognition apparatus is applied. An example of providing the emotional state of a user to an external device or user is described below with reference to FIG. 10.

Referring to FIG. 10, a terminal includes a display unit 1000. For example, the display unit 1000 may be a touch screen.

The display unit 1000 may include an emotion display module 1001. The emotion display module 1001 may include an internal emotion display 1010 and an external emotion display 1020. For example, referring to FIGS. 9 and 10, the emotion provision unit 902 may control a graphic effect so that the theme of a user interface (such as, for example, font, color, and the like) on the internal emotion display 1010 may automatically change according to the internal emotional state of a user. The emotion provision unit 902 may display the external emotional state of the user on the external emotion display 1020. In a further example, the emotion provision unit may transmit the external emotional state of the user to another terminal.

Figure 11:
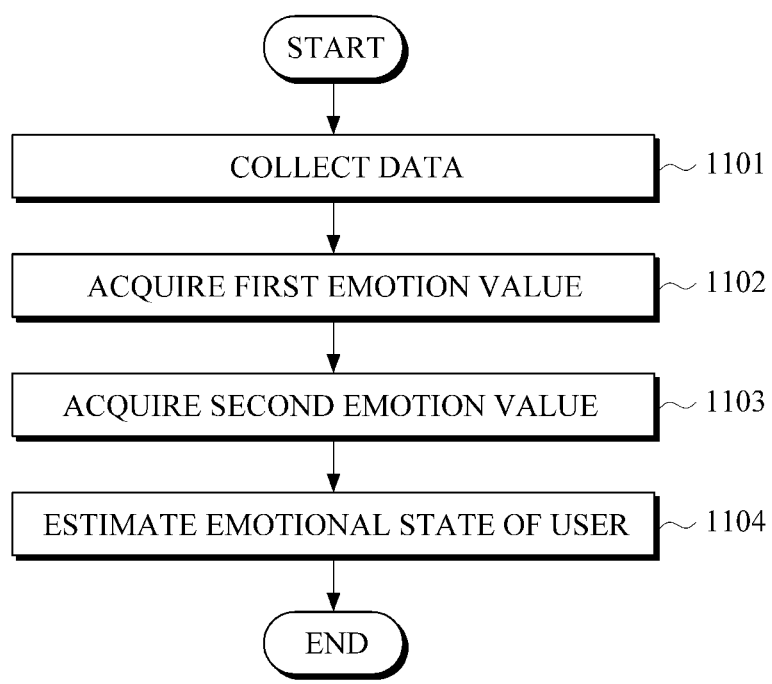
FIG. 11 is a flowchart illustrating an example of an emotion recognition method.

FIG. 11 illustrates an example of an emotion recognition method.

Referring to FIGS. 1 and 11, in operation 1101, the emotion recognition apparatus 100 collects sensing data from a terminal. For example, the data collection unit 101 may collect raw data from hardware and software sensors of the terminal.

In operation 1102, the emotion recognition apparatus 100 acquires a first emotion value based on the amount or intensity of the sensing data. For example, referring to FIG. 2, the first emotion value acquisition unit 102 may calculate an arousal value as the first emotion value according to Equations (1) through (3).

In operation 1103, the emotion recognition apparatus 100 acquires a second emotion value based on the meaning of the sensing data. For example, referring to FIGS. 3 and 4, the second emotion value acquisition unit 103 may calculate a valence value as the second emotion value according to Equations (4) through (6).

In operation 1104, the emotion recognition apparatus 100 estimates the emotional state of a user based on the first and second emotion values. For example, the emotion estimation unit 104 may estimate the emotional state of the user by mapping the first and second emotion values onto a 2D emotion model.

The estimated emotional state of the user may be provided to an external device. For example, the estimated emotional state of the user may be displayed on the touch screen of the terminal or may be transmitted to another terminal.

Figure 12:
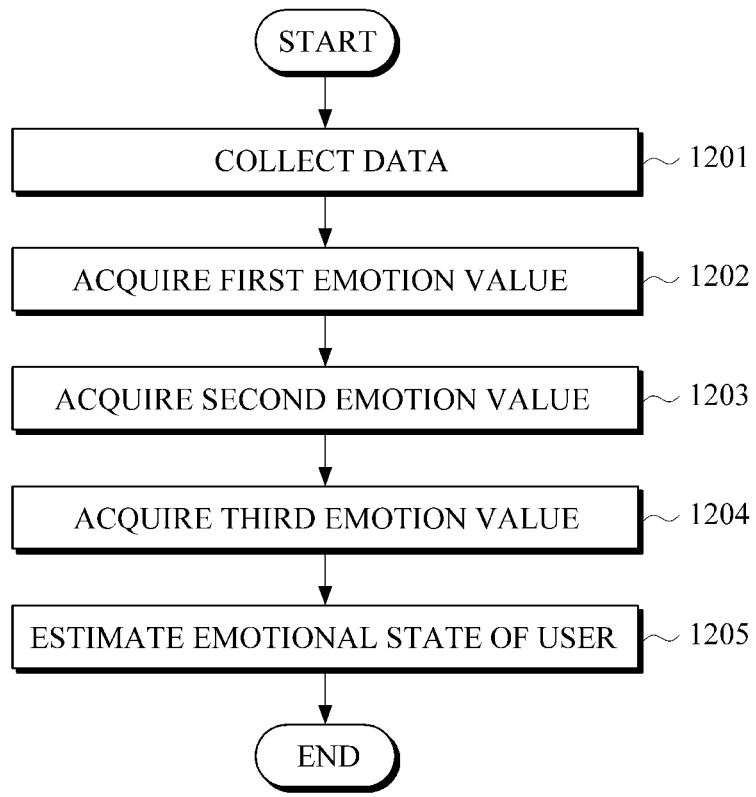
FIG. 12 is a flowchart illustrating another example of an emotion recognition method.

FIG. 12 illustrates another example of an emotion recognition method.

Referring to FIGS. 7 and 12, in operation 1201, the emotion recognition apparatus 700 collects sensing data from a terminal. For example, the data collection unit 701 may collect raw data from hardware and software sensors of the terminal.

In operation 1202, the emotion recognition apparatus 700 acquires a first emotion value based on the amount or intensity of the sensing data. For example, referring to FIG. 2, the first emotion value acquisition unit 102 may calculate an arousal value as the first emotion value according to Equations (1) through (3).

In operation 1203, the emotion recognition apparatus 700 acquires a second emotion value based on the meaning of the sensing data. For example, referring to FIGS. 3 and 4, the second emotion value acquisition unit 103 may calculate a valence value as the second emotion value according to Equations (4) through (6).

In operation 1204, the emotion recognition apparatus 700 acquires a third emotion value based on the user's personality trait. For example, the third emotion value acquisition unit 701 may acquire the third emotion value based on the user's personality trait with reference to the user personality DB 702.

In operation 1205, the emotion recognition apparatus 700 estimates the emotional state of the user based on the first and second emotion values or based on the first, second, and third emotion values. For example, the emotion estimation unit 704 may estimate the internal emotional state of the user by mapping the first and second emotion values onto a 2D emotion model. In another example, the emotion estimation unit 704 may estimate the external emotional state of the user by mapping the first, second, and third emotion values onto a 3D emotion model.

The estimated emotional state of the user may be provided to an external device. For example, the estimated internal emotional state of the user may be displayed on the touch screen of the terminal, or the estimated external emotional state of the user may be transmitted to another terminal.

For example, a 2D or 3D emotion model may be used to estimate the emotional state of a user. In another example, an emotional model customized for each individual user may be used. The emotional state of a user may be determined by probabilistically and statistically analyzing sensing data that is collected from a terminal. For example, if a user uses a predetermined application of a terminal, the user may be allowed to manually input his or her emotional state to the terminal. In this example, information on each emotional state of the user may continue to be collected as training data. The following table shows an example of training data.

| Character Input Speed | Frequency of Use of Backspace Key | Voice Input | Frequency of Input of Special Characters | Degree of Device Shake | Illumination | Location | Emotional State |
|---|---|---|---|---|---|---|---|
| High | High | False | High | High | Dark | Office | Sad |
| Medium | Medium | True | Low | Medium | Bright | On Way Home | Happy |

In response to the generation of the training data, the emotional state of the user in certain context may be probabilistically and statistically estimated by applying various machine learning algorithms, for example, a decision tree or Naive Bayes classifier.

A 2D or 3D emotion model may be determined based on training data customized for each individual user. For example, in a case in which a 3D vector (a, b, c) is given as an emotion factor, a personalized 3D emotion model may return different emotional states for the 3D vector (a, b, c) for different users.

As described above, the emotional state of a user may be estimated based on sensing data collected from a terminal, without a requirement of additional equipment.

The emotion recognition apparatus described herein may be implemented using hardware components and software components. For example, the data collection unit, emotion value acquisition units, emotion estimation unit, TA calculator, DM calculator, arousal calculator, input analyzer, context analyzer, valence calculator, and emotion provision unit. A processing device for executing operations of one or more of the units may be implemented using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors.

The software may include a computer program, a piece of code, an instruction, or some combination thereof, for independently or collectively instructing or configuring the processing device to operate as desired. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. In particular, the software and data may be stored by one or more computer readable recording mediums. The computer readable recording medium may include any data storage device that can store data which can be thereafter read by a computer system or processing device. Examples of the computer readable recording medium include read-only memory (ROM), random-access memory (RAM), CD-ROMs, magnetic tapes, floppy disks, optical data storage devices. Also, functional programs, codes, and code segments for accomplishing the example embodiments disclosed herein can be easily construed by programmers skilled in the art to which the embodiments pertain based on and using the flow diagrams and block diagrams of the figures and their corresponding descriptions as provided herein.

A number of examples have been described above. Nevertheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An emotion recognition apparatus, comprising:
a data collection unit configured to collect sensing data from a terminal;
a first emotion value acquisition unit configured to acquire a first emotion value corresponding to a first axis of a multidimensional emotion model based on an amount or an intensity of the sensing data;
a second emotion value acquisition unit configured to acquire a second emotion value corresponding to a second axis of the multidimensional emotion model based on a textual meaning of the sensing data; and
an emotion estimation unit configured to estimate an emotional state of a user based on the first emotion value and the second emotion value.

2. The emotion recognition apparatus of claim 1, wherein the first emotion value acquisition unit further acquires first-level data relating to the user's level of arousal by analyzing the amount or the intensity of the sensing data, and acquires the first emotion value based on the first-level data.

3. The emotion recognition apparatus of claim 1, wherein the first emotion value acquisition unit further calculates a touch activeness (TA) level by analyzing the amount or the intensity of sensing data relating to one or more touch inputs detected from the terminal, and calculates the first emotion value based on the calculated TA level.

4. The emotion recognition apparatus of claim 1, wherein the first emotion value acquisition unit further calculates a device movement (DM) level by analyzing the amount or the intensity of sensing data relating to the movement of the terminal, and calculates the first emotion value based on the calculated DM level.

5. The emotion recognition apparatus of claim 1, wherein the first emotion value acquisition unit further calculates a TA level by analyzing the amount or the intensity of sensing data relating to one or more touch inputs detected from the terminal, calculates a DM level by analyzing the amount or the intensity of sensing data relating to the movement of the terminal, and calculates the first emotion value based on a weighted sum of the calculated TA level and the calculated DM level.

6. The emotion recognition apparatus of claim 1, wherein the second emotion value acquisition unit further acquires second-level data relating to valence of the user by analyzing the meaning of the sensing data, and acquires the second emotion value based on the second-level data.

7. The emotion recognition apparatus of claim 1, wherein the second emotion value acquisition unit further calculates an input text (IT) level by analyzing the meaning of sensing data relating to a user input that is entered to the terminal, and calculates the second emotion value based on the calculated IT level.

8. The emotion recognition apparatus of claim 7, wherein the user input includes at least one selected from the group of text data, audio data, video data, and an emoticon.

9. The emotion recognition apparatus of claim 1, wherein the second emotion value acquisition unit further calculates a user context (UC) level by analyzing the meaning of sensing data relating to a context of the user, and calculates the second emotion value based on the calculated UC level.

10. The emotion recognition apparatus of claim 9, wherein the context includes at least one selected from the group of a location of the user, and a schedule of the user.

11. The emotion recognition apparatus of claim 1, wherein the second emotion value acquisition unit further calculates an IT level by analyzing the meaning of sensing data relating to a user input that is entered to the terminal, calculates a UC level by analyzing the meaning of sensing data relating to context of the user, and calculates the second emotion value based on a weighted sum of the calculated IT level and the calculated UC level,
wherein the user input includes at least one selected from the group of text data, audio data, video data, and an emoticon; and
wherein the context includes at least one selected from the group of a location of the user, and a schedule of the user.

12. An emotion recognition apparatus, comprising:
a data collection unit configured to collect sensing data from a terminal;
a first emotion value acquisition unit configured to acquire a first emotion value corresponding to a first axis of a multidimensional emotion model based on an amount or an intensity of the sensing data;
a second emotion value acquisition unit configured to acquire a second emotion value corresponding to a second axis of the multidimensional emotion model based on a meaning of the sensing data;
a third emotion value acquisition unit configured to acquire a third emotion value corresponding to a user's personality trait; and
an emotion estimation unit configured to estimate an emotional state of the user based on at least two selected from the group of the first emotion value, the second emotion value, and the third emotion value.

13. The emotion recognition apparatus of claim 12, wherein the first emotion value acquisition unit further acquires first-level data relating to the user's level of arousal by analyzing the amount or the intensity of the sensing data, and acquires the first emotion value based on the first-level data.

14. The emotion recognition apparatus of claim 12, wherein the first emotion value acquisition unit further calculates a TA level by analyzing the amount or the intensity of sensing data relating to one or more touch inputs detected from the terminal, and calculates the first emotion value based on the calculated TA level.

15. The emotion recognition apparatus of claim 12, wherein the first emotion value acquisition unit further calculates a DM level by analyzing the amount or the intensity of sensing data relating to the movement of the terminal, and calculates the first emotion value based on the calculated DM level.

16. The emotion recognition apparatus of claim 12, wherein the first emotion value acquisition unit further calculates a TA level by analyzing the amount or the intensity of sensing data relating to one or more touch inputs detected from the terminal, and calculates a DM level by analyzing the amount or the intensity of sensing data relating to the movement of the terminal, and calculates the first emotion value based on a weighted sum of the calculated TA level and the calculated DM level.

17. The emotion recognition apparatus of claim 12, wherein the second emotion value acquisition unit further acquires second-level data relating to valence of the user by analyzing the meaning of the sensing data, and acquires the second emotion value based on the second-level data.

18. The emotion recognition apparatus of claim 12, wherein the second emotion value acquisition unit further calculates an IT level by analyzing the meaning of sensing data relating to a user input that is entered to the terminal, and calculates the second emotion value based on the calculated IT level.

19. The emotion recognition apparatus of claim 18, wherein the user input includes at least one selected from the group of text data, audio data, video data, and an emoticon.

20. The emotion recognition apparatus of claim 12, wherein the second emotion value acquisition unit further calculates a UC level by analyzing the meaning of sensing data relating to a context of the user, and calculates the second emotion value based on the calculated UC level.

21. The emotion recognition apparatus of claim 20, wherein the context includes at least one selected from the group of a location of the user, and a schedule of the user.

22. The emotion recognition apparatus of claim 12, wherein the second emotion value acquisition unit further calculates an IT level by analyzing the meaning of sensing data relating to a user input that is entered to the terminal, calculates a UC level by analyzing the meaning of sensing data relating to context of the user, and calculates the second emotion value based on a weighted sum of the calculated IT level and the calculated UC level,
wherein the user input includes at least one selected from the group of text data, audio data, video data, and an emoticon; and
wherein the context includes at least one selected from the group of a location of the user, and a schedule of the user.

23. The emotion recognition apparatus of claim 12, wherein the emotion estimation unit further estimates an internal emotional state of the user based on the first and second emotion values, and estimates an external emotional state of the user based on the first, second, and third emotion values.

24. The emotion recognition apparatus of claim 23, further comprising:
an emotion provision unit to output data regarding the estimated internal emotional state and data regarding the estimated external emotional state of the user.

25. The emotion recognition apparatus of claim 24, wherein the emotion provision unit further outputs the data regarding the estimated internal emotional state of the user to a user interface of the terminal, and outputs the data regarding the estimated external emotional state of the user to an external device.

26. An emotion recognition method, comprising:
collecting sensing data from a terminal;
acquiring a first emotion value corresponding to a first axis of a multidimensional emotion model based on an amount or an intensity of the sensing data;
acquiring a second emotion value corresponding to a second axis of the multidimensional emotion model based on a textual meaning of the sensing data; and
estimating an emotional state of a user based on the first emotion value and the second emotion value.

27. An emotion recognition method, comprising:
collecting sensing data from a terminal;
acquiring a first emotion value corresponding to a first axis of a multidimensional emotion model based on an amount or an intensity of the sensing data;
acquiring a second emotion value corresponding to a second axis of the multidimensional emotion model based on a meaning of the sensing data;
acquiring a third emotion value corresponding to a user's personality trait; and
estimating an emotional state of the user based on at least two selected from the group of the first emotion value, the second emotion value, and the third emotion value.

28. The emotion recognition method of claim 27, wherein the estimating the emotional state of the user comprises:
estimating an internal emotional state of the user based on the first and second emotion values; and
estimating an external emotional state of the user based on the first, second, and third emotion values.

29. The emotion recognition method of claim 28, further comprising:
outputting the estimated internal emotional state and the estimated external emotional state of the user,
wherein the outputting of the estimated internal emotional state and the estimated external emotional state of the user comprises outputting the estimated internal emotional state of the user to a user interface of the terminal, and outputting the estimated external emotional state of the user to an external device.

30. The emotion recognition apparatus of claim 1, wherein the first emotion value and the second emotion value are values of Russell's emotion model.

31. The emotion recognition apparatus of claim 1, wherein the first emotion value and the second emotion value are values of Watson-Tellegen's emotion model.

32. The emotion recognition apparatus of claim 3, wherein the TA level is calculated with respect to a period of time for which a touch input is detected, touch counts detected during the period of time, a touch movement distance during the period of time, a heavy touch movement count during the period of time, and a number of characters entered during the period of time,
wherein the heavy touch movement count is calculated according to a number of substantially continuous touches that include more than a predetermined number of changes in direction.

33. The emotion recognition apparatus of claim 4, wherein the DM level is calculated with respect to a period of time for which a touch input is detected, a value representing x-axis acceleration of the terminal, a value representing y-axis acceleration of the terminal, and a value representing z-axis acceleration of the terminal.

34. The emotion recognition apparatus of claim 7, wherein the IT level is calculated with respect to a period of time for which a touch input is detected, a ratio of positive user inputs to all user inputs that are entered during the period of time, and a ratio of negative user inputs to all the user inputs that are entered during the period of time.

35. The emotion recognition apparatus of claim 9, wherein the UC level is calculated with respect to an elapsed time for a touch input, a duration for which the user remains at a location, a value representing positive or negative context of the location, and a value representing positive or negative context of a schedule of the user.

36. The emotion recognition apparatus of claim 1, wherein the first emotion value acquisition unit is configured to acquire the first emotion value based on a pattern of a user input using a physical contact with the terminal.

\* \* \* \* \*